US011871721B2

(12) United States Patent
Cousins

(10) Patent No.: US 11,871,721 B2
(45) Date of Patent: Jan. 16, 2024

(54) GRAPEVINES AND RELATED METHODS OF PRODUCTION AND USE

(71) Applicant: E & J Gallo Winery, Modesto, CA (US)

(72) Inventor: Peter Samuel Melugin Cousins, Modesto, CA (US)

(73) Assignee: E&J Gallo Winery, Modesto, CA (US)

( * ) Notice: Subject to any disclaimer, the term of this patent is extended or adjusted under 35 U.S.C. 154(b) by 382 days.

(21) Appl. No.: 17/064,977

(22) Filed: Oct. 7, 2020

(65) Prior Publication Data

US 2022/0104449 A1 Apr. 7, 2022

(51) Int. Cl.
*A01H 6/88* (2018.01)
*A01H 5/08* (2018.01)

(52) U.S. Cl.
CPC .............. *A01H 6/88* (2018.05); *A01H 5/08* (2013.01)

(58) Field of Classification Search
None
See application file for complete search history.

(56) References Cited

U.S. PATENT DOCUMENTS

| PP6,166 P | 5/1988 | Lider et al. |
| 9,706,726 B2 | 7/2017 | Bloodworth |

OTHER PUBLICATIONS

Jiao J, Fu X, Liu C, Fan X, Zhang Y and Jiang J, 2014, Mo. Breeding, DOI 10.1007/s1 1032-014-0124-1.*
Prince WR, 1830. Treatise On the Vine: History from the earliest ages to the present day.*
Popenoe AM and Mason SC, 1893, Experiment Station of the Kansas State Agriculture College, Manhattan, Bulletin No. 44.*
Ferreira V, Matus JT, Pinto-Carnide O, Carrasco D, Arroyo-Garcia R and Castro I. 2019. BMC Genomics, 20:952.*
Azuma A, Udo Y, Sato A, Mitani N, Kono A, Ban Y, Yakushiji H, Koshita Y and Kobayashi S. 2011. Theor Appl Genet, 122:1427-1438.*
USDA—Plant Inventory, 1996 (No. 204, Part I, p. 280).*
De Lorenzis, G. Mol Biotecnola2015) 57:265-274. (Year: 2015).*
De Lorenzis, et al., Zibibbo Nero Characterization, a Red-wine Grape Revertant of Muscat of Alexandria, Molecular Biotechnology 57(3): 265-274, 2015.
International Search Report regarding International App. No. PCT/US2021/052193, dated Jan. 25, 2022.
Liang et al., Inheritance of anthocyanin content in the ripe berries of a tetraploid x diploid grape cross population, Euphytica 186(2): 343-356, 2012.
Oberle, A Genetic Study of Variations in Floral Morphology and Function in Cultivated Forms of Vitis, Cornell University, Technical Bulletin 250, 1938.
Shuck et al., Obtaining interspecific hybrids, and molecular analysis by microsatellite markers in grapevine, Pomology Pesq. Agropec. Bras. 46 (11):1480-1488, 2011.
This et al., Wine grape (*Vitis vinifera* L.) color associates with allelic variation in the domestication gene VvmybA1, Theoretical and Applied Genetics 114(4):723-730, 2007.
Cadle-Davidson, Molly M., et al., "Genomic amplification of the Gret1 retroelement in white-fruited accessions of wild Vitis and interspecific hybrids," Theoretical and Applied Genetics 116, No. 8 (Mar. 12, 2008): 1079-1094.
Dunstan, R.T., "Hybridization of Euvitis x V. rotundifolia: Backcrosses to Muscadine," J. Am. Soc. Hortic. Sci. 84 (1964):238-242.
Jiao, Jian, et al., "Study of the relationship between the cultivars of Vitis vinifera and the white-fruited and hermaphrodite Chinese wild grapes," Molecular Breeding 34, No. 3 (2014): 1401-1411.
Lewter, Jennifer, et al., "High-density linkage maps and loci for berry color and flower sex in muscadine grape (*Vitis rotundifolia*)," Theoretical and Applied Genetics 132, No. 5 (Feb. 12, 2019): 1571-1585.
Stover. L. H. The Lake Emerald Grape, University of Florida Agricultural Experiment Stations. Circular S-68. Jan. 1954.
Cadle-Davidson et al. Genomic amplification of the Gret1 retroelement in white-fruited accessions of wild Vitis and interspecific hybrids. Theor Appl Genet (2008) 116:1079-1094.

* cited by examiner

*Primary Examiner* — Russell Kallis
(74) *Attorney, Agent, or Firm* — Dentons US LLP

(57) ABSTRACT

This disclosure relates to a white-fruited, perfect-flowered, bunch grapevine having white fruit due to a non-VvMybA1 genetic mutation. Methods for producing the grapevine can utilize or include, for example, breeding, mutagenesis, recombinant DNA, and/or gene editing. The grapevine can be used to obtain achieve new grape colors and/or new combinations of color and flavor.

10 Claims, 2 Drawing Sheets

GRAPEVINES AND RELATED METHODS OF PRODUCTION AND USE

TECHNICAL FIELD

The following disclosure relates to grapevines and, in certain examples, to methods for producing and using white-fruited, perfect-flowered, bunch grapevines.

BACKGROUND

There are two groups of grapevine species: bunch grapevines and muscadine grapevines. Bunch grapevines have a diploid chromosome number of 38 (e.g., 2n=2x=38) for wild species and most varieties (although there are some tetraploid varieties 2n=4x=76 and some aneuploid varieties), bark that sheds in strips or strings, and discontinuous stem pith due to nodal diaphragms. Bunch grapevine species include *Vitis vinifera* (a common and widespread cultivated wine, table, and raisin grape), *Vitis labrusca, Vitis aestivalis,* and *Vitis riparia*. The total number of bunch grape species is more than 60. Nearly all of the world's commercial grape production for any purpose (such as wine, table grape, raisin, or juice) is from bunch grapevines such as Cabernet Sauvignon, Chardonnay, Thompson Seedless, or Concord. Bunch grapevines are grown commercially in many countries and wild bunch grape species are native to Europe, Asia, Africa, North America, and South America.

The muscadine grapevines have a diploid chromosome number of 40 (2n=2x=40) for wild species and most varieties (e.g., some tetraploids are reported), bark that sheds in plates, and continuous stem pith due to the lack of nodal diaphragms. Commonly recognized muscadine grapevine species are *Vitis rotundifolia, Vitis munsoniana,* and *Vitis popenoei*. Three species of muscadine grapevines are reported. In contrast to bunch grapevines, commercial muscadine grapevine cultivation is limited to the southeastern United States and wild muscadine grape species are endemic to North America.

Bunch grapevine species and muscadine grapevine species are highly interfertile within each respective group, but creating hybrids between the groups is difficult because of the difference in chromosome number. Most bunch grape/muscadine grape hybrid vines are infertile or have low fertility; however, breeders have moved some traits from one group to the other group, such as stenospermocarpic seedlessness, bred from *Vitis vinifera* (a bunch grapevine) into *Vitis rotundifolia* (a muscadine grapevine). The genomes of bunch grapevines and muscadines may be similar in organization, such that genes known to impact a particular phenotype in one grape group may have a similar effect in the other grape group.

Grape color variation chiefly is due to differences in an amount and/or kind of anthocyanin pigments in the skin and/or pulp. Both bunch grapevines and muscadine grapevines have species or varieties with deeply colored black or purple skin, with red skin, and with yellow, green, or whitish skin. Varieties with deeply color black or purple skin usually are described as "black" for bunch grapevines, such as Cabernet Sauvignon wine grape (*Vitis vinifera*) and Autumn Royal table grape (*Vitis vinifera*) and called "purple" or "black" for muscadine grapevines such as Noble wine grape (*Vitis rotundifolia*) and Black Fry table grape (*Vitis rotundifolia*). Bunch grape varieties with red skin include Flame Seedless (*Vitis vinifera*) and Crimson Seedless (*Vitis vinifera*). Muscadine grape varieties with red skin include Scarlett (*Vitis rotundifolia*). Bunch grape varieties with pale skin with very low or absent anthocyanin content usually are described as "white", although the fruit color may be green, yellow, or white. White bunch grapevines include Chardonnay wine grape (*Vitis vinifera*) and Thompson Seedless table and raisin grape (*Vitis vinifera*). Muscadine grapevines with pale skin usually are described as "bronze" and the fruit color can be golden, bronze, or dark yellow. Bronze muscadine grapevines include Sterling wine grape (*Vitis rotundifolia*) and Fry table grape (*Vitis rotundifolia*).

Grape fruit color variation in bunch grapevines may be nearly all due to variation in the VvMybA1 gene (or its homologues in other species) on linkage group 2 of the grape genome. Nearly all of the white-fruited bunch grapevines belong to the species *Vitis vinifera* or are hybrids of *Vitis vinifera* that have inherited the fruit color locus from *Vitis vinifera*. For example, Chardonnay, Thompson Seedless, Princess, Sauvignon blanc, and Semillon are all *Vitis vinifera* varieties with white (that is, non-black and non-red) fruit color. Niagara, Cayuga White, and Seyval blanc are interspecific hybrid bunch grape varieties with white fruit and they and other varieties may have inherited the white fruit color allele from *Vitis vinifera*.

The difference between purple and bronze muscadine grapevines is determined by a different gene than is responsible for black, red, or white bunch grape fruit color variation. It has been demonstrated that muscadine grape fruit color variation may be due to gene differences at a locus that is located on the equivalent of *Vitis vinifera* bunch grape linkage group 4. The high degree of synteny between the muscadine grape genome and the bunch grape genome indicates that the purple/bronze muscadine grape color fruit difference is due to a different gene and locus than the black, red, or white bunch grape fruit color difference.

In bunch grapevines, the VvMybA1 alleles on linkage group 2 for colored fruit (e.g., either black or red) are dominant to the allele for white (e.g., non-colored) fruit. The allele(s) for white fruit are recessive to the alleles for colored fruit. When breeding new grapevine varieties, it is well recognized that a white-fruited bunch grapevine may have two colored parents (for example, Cabernet blanc which is the white-fruited progeny of Cabernet Sauvignon and Regent, both of which are black fruited) or a white-fruited grapevine may have one parent with colored fruit and one parent with black fruit (for example, Chardonnay, which is the white-fruited progeny of Pinot noir, which is black fruited, and Heunsich weiss, which is white-fruited).

When two white-fruited bunch grapevines are pollinated, cross-pollinated, or hybridized and the seedling is grown, it is expected that all of the offspring will be white-fruited. This is reported from many studies of cross pollination, hybridization, and self-pollination of white-fruited bunch grapevines, and is consistent with a model that in bunch grapevines the white fruit color is typically due to a VvMybA1 mutation. Any two white-fruited bunch grapevines with the same mutations or similar mutations may fail to genetically complement one another in crossing.

Nearly all wild species of bunch grapevines produce exclusively colored fruit, either black or red. Aside from *Vitis vinifera* and hybrids with *Vitis vinifera* ancestry, white-fruited accessions of three other bunch grape species may be reported in cultivation. White-fruited accessions may be reported from the wild bunch grape species *Vitis aestivalis, Vitis riparia,* and *Vitis labrusca*. Typically, vines of three species and all other wild bunch grape species produce colored (black or red), but these accessions are unusual because they produce white fruit. White-fruited individuals have been reported from other wild grape species, but this may be the result of species nomenclature issues or due to previously unrecognized hybridization with *Vitis vinifera*.

Wild bunch grapevines ordinarily bear functionally unisexual flowers and all of the flowers on one vine may be the same flower type. The flower types may be staminate or male, which produces viable pollen, but ordinarily does not produce fruit, and pistillate or female, which produces fruit, but ordinarily does not produce viable pollen. Vines of neither flower type are self-fertile and cross pollination from vine to vine is required in order to set fruit and produce viable seeds. In botanical terms, wild grape species are dioecious.

In contrast to wild bunch grapevines, nearly all cultivated bunch grape varieties bear functionally bisexual flowers with viable male (stamen) and female structures (pistil). In botanical terms, these bunch grape varieties are perfect, because perfect in botanical terms means having functional male and female parts in the same flower. In these bunch grape varieties, each flower is capable of producing viable pollen and developing into a fruit. The flowers are self-pollinating and each vine and variety can set fruit on its own without the requirement for cross-pollination by another vine or variety. For example, Chardonnay, Cabernet Sauvignon, Thompson Seedless, Muscat of Alexandria, and Sauvignon blanc bunch grape varieties are self-fertile and self-pollinating (these five example varieties are all *Vitis vinifera*). A few varieties of bunch grapevines produce grapes but are not self-fertile because these varieties are pistillate or female flowered and do not produce viable pollen. For example, Ohanes and Chaouch blanc bunch grape varieties (*Vitis vinifera*) and St. Pepin grape variety (*Vitis* interspecific hybrid) are pistillate or female flowered and are not self-fertile or do not self-pollinate. It is generally not convenient for grape growers to cultivate pistillate varieties because these varieties do not produce a commercial crop unless pollinated and so either the vines must be hand pollinated or the varieties must be mixed in a planting in order to ensure that the pistillate varieties are pollinated and produce a commercial crop. Perfect-flowered, self-pollinating varieties overwhelmingly dominate bunch grape production in all categories such as wine, table grape, juice grape, and raisin grape because the perfect-flowered, self-pollinating varieties are easier to grow since they do not require cross pollination.

There is a need for new bunch grapevine plants that are perfect-flowered and produce fruit having new colors and/or new combinations of color and flavor.

The foregoing discussion, including the description of motivations for some embodiments of the invention, is intended to assist the reader in understanding the present disclosure, is not admitted to be prior art, and does not in any way limit the scope of any of the claims.

SUMMARY

In certain examples, this disclosure relates to a white-fruited, perfect-flowered, bunch grapevines and methods of producing and using the grapevines. Compared to other white-fruited, perfect-flowered, bunch grapevines, such as Chardonnay, Sauvignon blanc, and Thompson Seedless, which are white-fruited due to VvMybA1 mutations, the white-fruited, perfect-flowered, bunch grapevines described herein can be white-fruited due to a non-VvMybA1 mutation. By comparison, while it is presently discovered that there are other bunch grapevines that are white-fruited due to a non-VvMybA1 genetic variation (e.g., *Vitis labrusca* Alba), these other grapevines are not perfect-flowered and self-fertile, like the grapevines described herein. Further, while there are other perfect-flowered, self-fertile grapevines that are non-colored (e.g., white-fruited or bronze-fruited), these other grapevines are muscadine grapevines, not bunch grapevines.

The grapevines described herein can be used to produce a wide variety of plant products, such as, for example, whole grapes, raisins, wine, juice, fruit leather, paste, puree, freeze-dried fruits, nutraceutical preparations, jam, or jelly. Methods for producing the grapevines can utilize or include, for example, breeding (e.g., hybridization, cross-pollination, self-pollination, open-pollination, and/or other methods), mutagenesis (e.g., chemical, radiation, transposon activation, tissue culture, ribonucleoprotein, and/or other methods), recombinant DNA approaches, gene editing, or any combination thereof.

Advantageously, the grapevines described herein can be used to produce grapes and grape products that have new colors and/or new combinations of color and flavor/aroma. For example, in many or all existing grape product categories there is a recognized relationship between color and flavor/aroma—black grapes make red wine that smells like cherries and white grapes make white wine that smells like peaches or apricots. It is presently discovered, however, that the pigments that drive the color of the grapes and wine may not themselves be flavor or aroma-impactful at concentrations found in the grapes or wine. Advantageously, the grapevines and methods described herein are able to achieve new mutations in an anthocyanin biosynthesis pathway of the grape genome, such that the relationships between color, flavor, and aroma may be better understood and reorganized to create new combinations. The grapevines can be used, for example, to produce white wines that taste like red wines.

In general, in one aspect, the subject matter of this disclosure relates to a method of producing a grapevine. The method includes: breeding a first grapevine with a second grapevine to produce grapevine offspring, wherein the first grapevine is a non-perfect-flowered, bunch grapevine having white fruit due to a non-VvMybA1 mutation, and wherein the second grapevine is a perfect-flowered, bunch grapevine; and breeding the grapevine offspring to obtain a white-fruited, perfect-flowered, bunch grapevine having white fruit due to the non-VvMybA1 mutation.

In certain examples, the first grapevine can be pistillate-flowered. The first grapevine can be, for example, *Vitis labrusca* Alba. The second grapevine can be a white-fruited, perfect-flowered bunch grapevine, and the grapevine offspring can be black-fruited. The second grapevine can be, for example, Muscat of Alexandria, Chardonnay, Thompson Seedless, Princess, Emerald Seedless, Emerald Riesling, Seyval blanc, Cayuga White, Selma Pete, Malvasia bianca, Sauvignon blanc, Chenin blanc, Monbadon, Airen, Melody, Himrod, Romulus, Frontenac blanc, Perlette, Delight, Gold, Lake Emerald, Aligote, Pinot blanc, Villard blanc, Vidal blanc, Canada Muscat, Triplett blanc, Muscat blanc, DOVine, Fiesta, Autumn Seedless, Fuji Muscat, Baco blanc, Centennial Seedless, Dakapo, Ruby Cabernet, or Ruby Seedless. The grapevine offspring can be or include a perfect-flowered, bunch grapevine. Each breeding step can be or include hybridization, cross pollination, self-pollination, and/or open-pollination. Breeding the grapevine offspring can include breeding the grapevine offspring with the first grapevine. Breeding the grapevine offspring can include self-pollination or crossing the grapevine offspring with a sibling of the grapevine offspring. The method can include reproducing the white-fruited, perfect-flowered, bunch grapevine from at least one of a seed, a cutting, a graft (or grafting), an air layer (or air layering), or a tissue culture.

In another aspect, the subject matter of this disclosure relates to a white-fruited, perfect-flowered, bunch grapevine having white fruit due to a non-VvMybA1 mutation. The white-fruited, perfect-flowered, bunch grapevine can have a pedigree including a non-perfect-flowered, bunch grapevine having white fruit due to the non-VvMybA1 mutation. The white-fruited, perfect-flowered, bunch grapevine can have a pedigree including a black-fruited grapevine obtained by breeding two white-fruited grapevines. The non-VvMybA1 mutation can be achieved using mutagenesis, recombinant DNA, and/or gene editing.

In another aspect, the subject matter of this disclosure relates to a tissue culture produced from protoplasts or cells from a white-fruited, perfect-flowered, bunch grapevine having white fruit due to a non-VvMybA1 mutation, wherein the cells or protoplasts are produced from a plant part including at least one of leaf, pollen, ovule, embryo, cotyledon, hypocotyl, meristematic cell, root, root tip, petal, stamen, pistil, anther, flower, berry, seed, shoot, stem, or petiole. The tissue culture can be used to regenerate a grapevine plant.

In another aspect, the subject matter of this disclosure relates to a method of producing a commodity plant product. The method includes: obtaining a white-fruited, perfect-flowered, bunch grapevine having white fruit due to a non-VvMybA1 mutation, or a part thereof; and producing the commodity plant product from the plant or a portion thereof, wherein the commodity plant product includes at least one of whole grapes, raisins, wine, juice, fruit leather, paste, puree, freeze-dried fruits, nutraceutical preparations, jam, or jelly.

In another aspect, the subject matter of this disclosure relates to a method of producing a grapevine. The method includes: obtaining a black-fruited, perfect-flowered, bunch grapevine; and altering a gene in an anthocyanin biosynthesis pathway of the grapevine using at least one of mutagenesis, recombinant DNA, or gene editing to derive a white-fruited, perfect-flowered, bunch grapevine having white fruit due to a non-VvMybA1 mutation.

These and other objects, along with advantages and features of embodiments of the present invention herein disclosed, will become more apparent through reference to the following description, the figures, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DETAILED DESCRIPTION

It is contemplated that apparatus, systems, methods, and processes of the claimed invention encompass variations and adaptations developed using information from the embodiments described herein. Adaptation and/or modification of the apparatus, systems, methods, and processes described herein may be performed by those of ordinary skill in the relevant art.

It should be understood that the order of steps or order for performing certain actions is immaterial so long as the invention remains operable. Moreover, two or more steps or actions may be conducted simultaneously.

In various examples, "white-fruited" or "non-colored" can refer to grapes that are white, yellow, amber, gold, and/or green when mature, for example, due to an absence or reduced amount of anthocyanin pigments.

In various examples, "black-fruited" or "colored" can refer to grapes that are black, blue, red, and/or purple when mature, for example, due to a presence or increased amount of anthocyanin pigments (e.g., compared to white-fruited grapes).

In various examples, "qualitative differences" can refer to a categorical difference in color between colored grapes and non-colored grapes, for example, resulting from different amounts of anthocyanin pigments. In some instances, a qualitative difference in color can be associated with a change in hue (e.g., from red to green).

In various examples, "quantitative differences" can refer to continuous variations in color intensity that can occur among colored grapes (e.g., from light red to dark red) or among non-colored grapes (e.g., from light green to dark green). Such differences in color can be due to, for example, variations in an amount of anthocyanin pigments present in different colored grape varieties.

In various examples, "perfect-flowered" or "perfect" can refer to flowers that have functional male (stamen) and female (pistil) parts or structures in the same flower. "Non-perfect-flowered" or "non-perfect" can refer to flowers that do not have functional male and female parts in the same flower. Non-perfect flowers can be, for example, pistillate flowers or staminate flowers.

In various examples, "VvMybA1" can refer to a transcription factor on linkage group 2 of the grape genome of *Vitis vinifera* and/or homologues of VvMybA1 found in other bunch grape species (e.g., that are regularly interfertile with *Vitis vinifera*). Genetic mutations of VvMybA1 can produce qualitative differences in fruit color (e.g., colored versus non-colored).

Figure 1:
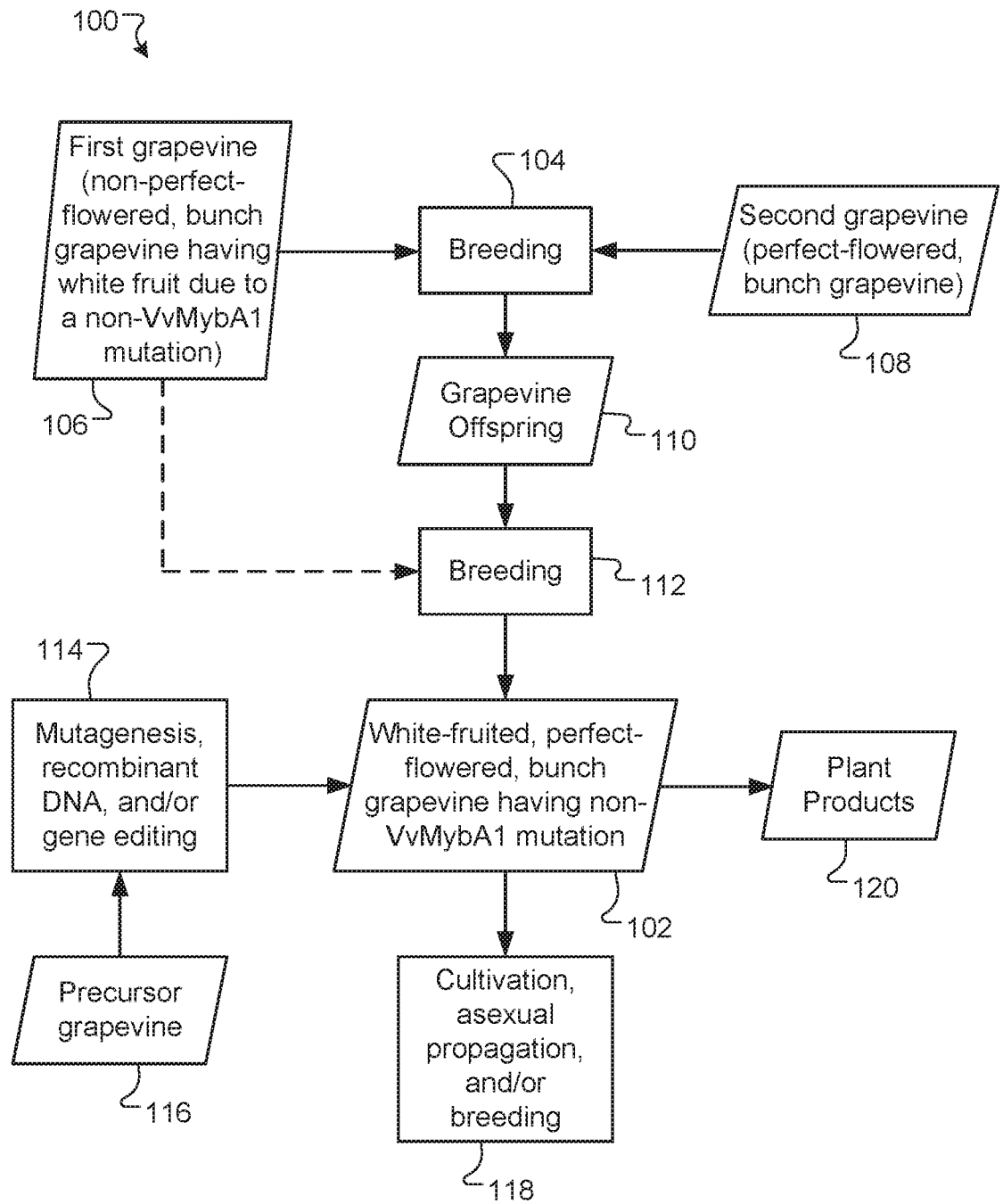
FIG. 1 is schematic diagram illustrating methods of producing and using a white-fruited, perfect-flowered, bunch grapevines having white fruit due to a non-VvMybA1 mutation, according to an exemplary embodiment.

FIG. 1 is a schematic diagram of example methods 100 of producing and using a white-fruited, perfect-flowered, bunch grapevine 102 having white fruit due to a non-VvMybA1 mutation. As illustrated in the examples that follow, the grapevine 102 can be produced by breeding (step 104) a first grapevine 106 with a second grapevine 108 to produce grapevine offspring 110. The first grapevine 106 can be, for example, a non-perfect-flowered, bunch grapevine having white fruit due to the non-VvMybA1 mutation. The second grapevine 108 can be, for example, a perfect-flowered, bunch grapevine and can be black-fruited or white-fruited (e.g., due to a VvMybA1 mutation). Once obtained, the grapevine offspring 110 can be self-pollinated or crossed (step 112) (e.g., with the first grapevine 106) to produce the grapevine 102. Alternatively or additionally, the grapevine 102 can be produced by performing mutagenesis, recombinant DNA, and/or gene editing (step 114) on a precursor grapevine 116, such as, for example, a black-fruited, perfect-flowered, bunch grapevine (e.g., *Vitis vinifera* Merlot), as described herein. The grapevine 102 can be cultivated, propagated asexually, and/or used in breeding (step 118). Alternatively or additionally, the grapevine 102 can be used to produce plant products 120, such as, for example, whole grapes, raisins, wine, juice, fruit leather, paste, puree, freeze-dried fruits, nutraceutical preparations, jam, or jelly.

Example 1

In one example, the pistillate (e.g., not self-fertile) flowers of *Vitis labrusca* Alba (United States Department of Agriculture, National Plant Germplasm System Plant Introduction 588165, abbreviated as PI 588165) vines were pollinated with pollen from two perfect-flowered self-fertile white-fruited varieties of *Vitis vinifera* (pollen parent varieties), one of which was *Vitis vinifera* Muscat of Alexandria. Both of the pollen parent varieties are understood to have VvMybA1 mutations that are responsible for the white fruit color. The combination of the seed parent with each pollen parent made a distinct cross and population, and the distinct identity of the crosses, populations, and individuals within the populations was maintained throughout seed collection and planting, and seedling germination, cultivation, and characterization.

The seedlings from these crosses were fully fruiting about two years later and it was observed that all of the seedlings had colored fruit, which is unexpected and surprising since the parents of both populations had white or non-colored fruit. This observation demonstrates genetic complementation. For example, because the pollen parents have VvMybA1 mutations that are responsible for the white fruit color of the pollen parent varieties, it is presently surmised that *Vitis labrusca* Alba has a mutation or genetic variation in a different gene (e.g., a non-VvMybA1 gene). Because colored fruit was observed on all of the multiple seedlings from the sexual hybridization of two white-fruited parents in two populations, this general phenomenon was found to be consistent and repeatable.

Example 2

In one example, bunch grape sources of white fruit not due to genetic variation in VvMybA1 can be used for hybridization and breeding to create white-fruited, perfect-flowered grapevines. *Vitis labrusca* Alba is a white-fruited bunch grape with pistillate flowers that are functionally female. *Vitis labrusca* Alba is not self-fertile but is cross-fertile through hybridization with other bunch grapes, which means that when *Vitis labrusca* Alba is pollinated by other bunch grapes it can set viable seeds that grow into fertile plants. When *Vitis labrusca* Alba was crossed to *Vitis vinifera* varieties with perfect flowers and with white fruit known to be due to genetic variation in VvMybA1, the seedlings all bore colored fruit, consistent with Example 1. The hybrid seedlings of *Vitis labrusca* Alba crossed with *Vitis vinifera* were successfully cultivated in a vineyard and some were used in additional generations of breeding and hybridization which resulted in more seedlings. This is consistent with the *Vitis labrusca* Alba as a genetic source of white fruit not due to genetic variation in VvMybA1, as presently discovered and described herein. *Vitis labrusca* Alba can be hybridized successfully with perfect flowered bunch grapes, and viable, fertile seedlings can be produced from the hybridization.

In general, *Vitis labrusca* is a naturally occurring wild bunch grapevine species that is native to the United States. This species has been reported to occur in nature both in colored fruit types (e.g., black, blue, purple, or red fruit) and in white or non-colored fruit types. *Vitis labrusca* Alba specifically is one source of white fruit due to genetic variation not in VvMybA1, and there may be other *Vitis labrusca* vines that have white fruit due to the same or similar genetic variation as *Vitis labrusca* Alba. Such other *Vitis labrusca* vines may be expected to have the same genetic and physiological fruit color attributes. For example, these other vines might be related to *Vitis labrusca* Alba and may share the same genetic mutation by descent or origin, or these vines might have the same genetic variation from independent origin. Additionally or alternatively, there may be other *Vitis labrusca* vines that have white fruit due to genetic variation not in VvMybA1 and/or that have mutations in different genes (e.g., compared to the genetic mutations of *Vitis labrusca* Alba).

Other bunch grapevine species have been reported to have white-fruited forms or vines, including *Vitis riparia, Vitis aestivalis*, and *Vitis mustangensis*. White-fruited vines may be occurring in any bunch grapevine species due to genetic variation in VvMybA1 (or its homologues in other species) or due to genetic variation in other genes. If the white fruit is due to genetic variation not in VvMybA1 then such vines can be incorporated into a perfect-flowered bunch grapevine, as described herein, through cross-breeding or hybridization, because bunch grapevine species are generally inter-fertile.

Example 3

In one example, a white-fruited, perfect-flowered bunch grapevine having white fruit due to genetic variation not in VvMybA1 can be produced through crossing, hybridization, or other breeding method. It is expected that white fruit due to a genetic variation not in VvMybA1 can behave as a recessive mutation.

First, a bunch grape source of white fruit due to genetic variation not in VvMybA1 can be identified. The bunch grape source can be a variety, seedling, population, or other germplasm. To show that the white fruit color is due to genetic variation not in VvMybA1, a genetic complementation test can be conducted through hybridization, the genetic sequences can be compared, or other suitable genetic test or analysis method can be used. The bunch grape source of white fruit due to genetic variation not in VvMybA1 can be, for example, *Vitis labrusca* Alba.

The genetic source of white fruit can then be crossed or hybridized to a breeding partner. The breeding partner can be a different variety that has useful attributes and desirable alleles. The precise choice of a breeding partner can depend on the goals of the breeding program. For example, for a table grape or raisin grape breeding program the breeding partner may be seedless, and for a wine grape breeding program the breeding partner may have suitable wine quality. The breeding partner is preferably a perfect-flowered bunch grapevine, though other types of grapevines may be used. The breeding partner can have fruit of any color (e.g., red or white). The breeding partner can be any suitable bunch grape variety, such as, for example, *Vitis vinifera* Ruby Cabernet, Muscat of Alexandria, Thompson Seedless, Ruby Seedless, Dakapo, Muscat of Alexandria, Chardonnay, Thompson Seedless, Princess, Emerald Seedless, Emerald Riesling, Seyval blanc, Cayuga White, Selma Pete, Malvasia bianca, Sauvignon blanc, Chenin blanc, Monbadon, Airen, Melody, Himrod, Romulus, Frontenac blanc, Perlette, Delight, Gold, Lake Emerald, Aligote, Pinot blanc, Villard blanc, Vidal blanc, Canada Muscat, Triplett blanc, Muscat blanc, DOVine, Fiesta, Autumn Seedless, Fuji Muscat, Baco blanc, or Centennial Seedless.

In certain examples, the identified bunch grape source of white fruit due to a genetic variation not in VvMybA1 can be pistillate flowered. For example, the non-VvMybA1 mutations that give qualitative variation in fruit color can come from non-*Vitis vinifera* species that are not self-fertile and/or in which the vines are dioecious. A genetically white-fruited vine can be simple to identify by visually examining the fruit. A white-fruited vine from a wild bunch grapevine species is likely to be pistillate-flowered.

In some instances, however, a bunch grapevine can be staminate-flowered (male flowered) and can carry a mutation in a non-VvMybA1 gene that would result in white fruit. While the fruit color genetics of a staminate vine can be concealed because the staminate vine is fruitless, genetic sequencing or test crossing can be used to reveal that a staminate vine is carrying a white fruit color allele or, alternatively, plant growth regulator applications can be used to induce pistil growth in staminate flowers and produce fruit on a staminate vine. The staminate vine having the non-VvMybA1 mutation can then be used as a crossing or hybridization partner in breeding, as described herein. In bunch grapes, staminate flower type can be genetically dominant to other flower types and the breeding design can be modified, as needed.

In various examples, the seedlings from a first generation cross can have a parent with the novel white fruit due to a genetic variation not in VvMybA1 as one parent and the breeding partner as the other parent. Because of complementation and because the mutations are expected to be recessive, none of the first generation seedlings may have the novel white fruit color. The first generation seedlings should, however, inherit one copy of the non-VvMybA1 mutant allele from the parent carrying that mutation and the first generation seedlings could inherit perfect flowers and self-fertility from the other parent.

If the cross is made between a pistillate vine with white fruit due to genetic variation not in VvMybA1 and a perfect-flowered, self-fertile vine that is white fruited due to a VvMybA1 mutation, the first generation seedlings can all have colored fruit. The flower type of such first generation seedlings can be 100% perfect-flowered and self-fertile or 50% perfect-flowered and self-fertile and 50% pistillate (not self-fertile). The possible difference in flower type ratios can depend on whether the perfect-flowered, self-fertile parent is homozygous or heterozygous for the perfect flower allele.

If the cross is made between a staminate vine and a perfect-flowered vine, the first generation seedlings population can be expected to segregate 50% staminate and 50% fruitful. The fruitful vines may be all perfect-flowered and self-fertile or 50% perfect-flowered and self-fertile and 50% pistillate (not self-fertile), depending on the genetic composition of the perfect-flowered vine.

The following two scenarios include exemplary step-wise procedures for developing a white-fruited, perfect-flowered bunch grapevine, as described herein. An allele model uses the following symbolic representation, in which capital letters denote dominant alleles: for the VvMybA1 locus alleles, B=colored fruit, and b=white fruit; for the non-VvMybA1 fruit color locus alleles, A=colored fruit, and a=white fruit; and for flower type alleles, H=perfect flowers, and h=pistillate flowers.

Scenario 1

The allele model representation of *Vitis labrusca* Alba and *Vitis vinifera* Dakapo can be as follows: *Vitis labrusca* Alba=a a B B h h, and *Vitis vinifera* Dakapo—A A B B H h.

To begin, *Vitis labrusca* Alba (a pistillate, seed parent) can be hybridized or crossed with *Vitis vinifera* Dakapo (a perfect-flowered, black-fruited, pollen parent). The first generation seedlings can be black-fruited with the following genotypes: A a B B H h or A a B B h h. In some instances, similar black-fruited seedlings can be obtained by crossing *Vitis labrusca* Alba with other homozygous B B varieties, such as *Vitis vinifera* Lagrein, *Vitis vinifera* Ruby Cabernet, *Vitis vinifera* Graciano, and *Vitis vinifera* Durif. More generally, a bunch grapevine that does not have the same color gene mutation as *Vitis labrusca* Alba (e.g., a non-VvMybA1 mutation) can produce black-fruited seedlings when crossed to *Vitis labrusca* Alba. Further, given that nearly all bunch grape color variation can be due to VvMybA1 genetic variation, nearly all bunch grapevines can produce black-fruited offspring when crossed to *Vitis labrusca* Alba.

Next, *Vitis labrusca* Alba can be hybridized or crossed with a perfect-flowered, first generation seedling (e.g., A a B B H h) to create a second generation, which may segregate for novel white fruit color (e.g., due to non-VvMybA1 mutation) and flower type, as follows: ¼ of the second generation seedlings are black-fruited pistillate having genotype AaBBhh, ¼ of the second generation seedlings are white-fruited pistillate having genotype aaBBhh, ¼ of the second generation seedlings are black-fruited perfect-flowered having genotype A a B B H h, and ¼ of the second generation seedlings are white-fruited perfect-flowered having genotype a a B B H h. Perfect-flowered grapevines can be preferred to achieve self-fertility. The seedlings of the last genotype (A a B B H h) can be used to produce white-fruited, perfect-flowered, self-fertile bunch grapevines having white fruit color due to a non-VvMybA1 mutation, as described herein.

Scenario 2

To begin, *Vitis labrusca* Alba (a pistillate, seed parent) can be hybridized or crossed with *Vitis vinifera* Dakapo (a perfect-flowered, pollen parent), as described above for Scenario 1. This can result in first generation seedlings that are black-fruited with the following genotypes: A a B B H h or A a B B h h.

Next, a perfect-flowered first-generation seedling (genotype A a B B H h) is chosen and self-pollinated or crossed with a sibling having the same genotype (A a B B H h) to create a second generation, which may segregate for novel white fruit color (non-VvMybA1) and flower type, as follows: 9/16 of the second generation seedlings are black-fruited and perfect-flowered having genotypes A A B B H H, A A B B H h, A a B B H h, and A a B B H H, 3/16 of the second generation seedlings are black-fruited and pistillate having genotypes A A B B h h and A a B B h h, 1/16 of the second generation seedlings are white-fruited and pistillate having genotype a a B B h h, 3/16 of the second generation seedlings are white-fruited and perfect-flowered in which ⅓ have genotype a a B B H H and ⅔ have genotype a a B B H h. The seedlings of the last genotype (a a B B H H and/or a a B B H h) can be used to produce white-fruited, perfect-flowered, self-fertile bunch grapevines having white fruit color due to a non-VvMybA1 mutation.

Example 4

The novel combination of perfect flowers, self-fertile bunch grapevines that are white-fruited due to a non- VvMybA1 mutation (that is, a mutation complementary to VvMybA1) can be demonstrated or validated in several ways. For example, perfect flowers can be demonstrated by examining the flowers for the presence of functional pistils that develop into fleshy fruits and for the presence of functional stamens that produce viable pollen. Erect stamens on a grapevine flower typically indicate functionality. Pollen viability can be evaluated by pollinating another grapevine and observing the development of fruit or seeds, by germinating pollen in vitro, and/or by self-pollination.

Additionally or alternatively, self-fertility can be evaluated by bagging a cluster before anthesis in order to exclude other sources of pollen and determining if there is fruit set and fruit development. If there is fruit set and fruit development, this indicates self-fertility.

Additionally or alternatively, to determine if a vine is white-fruited, the mature fruit can be evaluated by examining the fruit color visually, such as by comparing the fruit color to a color chart. In some instances, the fruit color can be compared to the mature fruit of bunch grape varieties that are known to be non-colored or white, such as, for example, Muscat of Alexandria, Muscat blanc, Chardonnay, Colombard, Sauvignon blanc, Riesling, Pinot blanc, Trebbiano Toscano, Calmeria, Almeria, Thompson Seedless (synonym Sultanina), Princess, Niagara, Fiesta, Selma Pete, Autumn King, Autumn Seedless, Perlette, Gold, Aromella, Villard blanc, Himrod, Interlaken, Romulus, Malvasia Bianca, Cayuga White, Seyval blanc, Swenson White, and Triplett blanc, among others. In certain examples, the fruit color can be compared to the fruit of non-colored (e.g., bronze or white) fruited varieties of muscadine grapes, such as Fry, Scuppernong, Sterling, Tara, Hall, or Triumph, among others. Fruit color can be determined by measuring the anthocyanin content of the fruit using analytical chemistry methods, and the measured anthocyanin content can be compared to similar measurements obtained for other grape varieties having white and/or colored fruit.

To demonstrate that a non-VvMybA1 mutation is responsible for white fruit in a novel white-fruited grapevine, a genetic test for complementation can be performed through hybridization. For example, the white-fruited variety can be crossed or hybridized with a different variety known to carry the VvMybA1 mutation that gives white fruit. If the resulting seedlings are all black fruited, then the novel white-fruited grapevine can have a mutation that is not in VvMybA1. For example, the hybridization of *Vitis labrusca* Alba (white-fruited) with *Vitis vinifera* Muscat of Alexandria (white-fruited) was found to produce all black-fruited seedlings. Because Muscat of Alexandria is known to have the VvMybA1 mutation, the complementation observed in the black-fruited seedlings indicates that *Vitis labrusca* Alba has a mutation in a different gene (not a mutation in VvMybA1). Another method of determining that a non-VvMybA1 mutation is responsible for white fruit can involve sequencing all or part of the genomes or of the genes that control or influence grapevine fruit color. By examining and comparing gene sequences, mutations can be identified in non-VvMybA1 genes that may be responsible for causing white fruit (a qualitative mutation in fruit color).

Example 5

In certain examples, one or more genes in the anthocyanin biosynthesis pathway can be the target for mutagenesis, gene editing, breeding, recombinant DNA, or other practices to implement or achieve the non-VvMybA1 mutation responsible for white fruit. Genes that are identified for research, tracking, editing, mutation, or other activity can be candidates genes in the anthocyanin biosynthesis pathway. These genes can be responsible for the creation, production, development, transport, and alteration of anthocyanins and/or anthocyanin precursor molecules. The anthocyanin biosynthesis pathway can be consistent or conserved across many plant species. Candidate genes may be identified in grapevines based on genetic and functional studies in other plant species. In some cases, the anthocyanin biosynthesis pathway genes can be characterized for function and expression in grapevine.

Knowledge of the anthocyanin biosynthesis pathway genes, their function, and sequence in grapevine can be used to identify targets for genetic modification or genetic improvement through various methods, as described herein. Knowledge of the anthocyanin biosynthesis pathway and corresponding genes enables the tracking and validation of genetic modification, for example, to determine if genetic modification steps have been successful and/or to track genetic mutations across propagation generations (by sexual propagation such as seeds, by cutting, grafting, budding, tissue culture, or other methods of propagation).

White fruit mutant alleles in grapevine appear to be recessive and/or can be associated with a loss or change of function. When the candidate anthocyanin biosynthesis genes are characterized and the sequence and function of the genes are known, this facilitates the targeting of these genes to create new loss or change of function mutations that can result in white-fruited grapevines due to genetic variation in non-VvMybA1 genes.

In some implementations, the grapevine anthocyanin biosynthesis genes can be tracked through generations of breeding (e.g., crossing or hybridization) to predict or determine the inheritance of the white fruit allele that is caused by a mutation in a non-VvMybA1 gene. The anthocyanin biosynthesis gene sequence or nearby sequences can be used to develop a DNA marker that indicates the presence of the white fruit allele that is caused by a mutation in a non-VvMybA1 gene. Since it is expected that the mutations that result in white fruit will be recessive, a DNA marker that indicates the presence of the white fruit allele can be useful since visual inspection of the plant may not show a qualitative difference. In populations of black-fruited seedlings segregated for the presence of the white fruit allele, a DNA marker can be used to identify those seedlings that carry the white fruit allele. Additionally or alternatively, a DNA marker can be used to identify the fruit color of seedlings before the fruit develops, thereby enabling the breeder to enrich populations for the trait of white fruit that is due to genetic variation in a non-VvMybA1 gene. DNA markers can be used in grape breeding on small seedlings less than one month old to predict adult plant phenotypes that may not manifest for more than two years. The DNA marker for white fruit color can be used in combination with other DNA markers such as a flower type marker and/or markers for pest or disease resistance or other traits, to increase the likelihood of combining desirable traits in seedlings.

Genes in the anthocyanin biosynthesis pathway that are targets for genetic modification and for use in breeding include but are not limited to genes and gene families associated with achieving or producing the following functions, substances, or identities: leucoanthocyanidin dioxygenase, chalcone synthase, chalcone isomerase, dihydroflavonol 4-reductase, flavanone 3-hydoxylase, phenylalanine ammonia-lyase, cinnamate 4-hydroxylase, stilbene synthase, 4-coumarate:CoA ligase, glutathione S-transferase, Myb transcription factor family (excepting VvMybA1), multidrug resistance-associated protein, and/or UDP-glucose:flavonoids 3-O-glucosyltransferase.

Example 6

In some examples, recombinant DNA methods can be used to create a perfect-flowered bunch grapevine with white fruit due to genetic variation not in VvMybA1. In recombinant DNA methods, a DNA sequence can be introduced into the grapevine genome through recombination, which can be implemented through *Agrobacterium* co-cultivation, biolistic bombardment, or other methods. The introduced DNA sequence can be referred to as a transgene. The transgene can be introduced into one or a few cells of the grapevine and then a new grapevine can be cultivated with the transgene throughout the plant. The transgene can be stably integrated into the grapevine genome and maintained as a part of the genome through asexual propagation (e.g., cuttings, budding, and/or grafting) and/or sexual propagation (e.g., seeds and/or pollen). The transgene can have the function of qualitatively decreasing the anthocyanin in the mature grape, thereby creating a novel white fruit phenotype. The method can be used to decrease the function of a gene (other than VvMybA1) by, in effect, breaking, silencing, or changing the gene in such a manner that the anthocyanin in the mature fruit is qualitatively reduced and the new fruit color is white. The transgene can implement changes through antisense or RNA interference mechanisms or through some other mechanism.

For example, *Vitis vinifera* Ruby Cabernet is a black-fruited, perfect-flowered bunch grapevine variety. A transgene can be introduced to Ruby Cabernet that causes a loss of function of a glutathione S-transferase gene through RNA interference and the result can be a perfect-flowered bunch grapevine with white fruit due to a non-VvMybA1 mutation. This new vine can be cultivated, propagated asexually, and/or used in breeding.

Example 7

In some implementations, gene editing methods can be used to induce DNA sequence changes in grapevine genes other than VvMybA1, to create a white-fruited perfect-flowered bunch grapevine. The gene editing methods can include, for example, CRISPR/Cas9, zinc-finger nuclease, transcription activator-like effector nuclease, and other methods. The gene editing methods may not introduce new DNA sequences to the grape genome but may instead change the original DNA sequence to a new, desired sequence. The desired sequence can be a change in an anthocyanin biosynthesis gene that results in a qualitatively white-fruited grapevine. Gene editing can be used to change individual nucleotides or a group of nucleotides or to induce deletions, insertions, rearrangements, or other kinds of mutations, and such changes can have the effect of qualitatively decreasing the amount of anthocyanin in the mature fruit, thereby creating a white-fruited grapevine.

For example, *Vitis vinifera* Cabernet Sauvignon is a black-fruited, perfect-flowered bunch grapevine variety. Gene editing through CRISPR/Cas9 in Cabernet Sauvignon can be conducted in a glutathione S-transferase gene to convert a functional codon into a premature stop codon and the result can be a perfect-flowered bunch grapevine with white fruit due to a non-VvMybA1 mutation. This new vine can be cultivated, propagated asexually, or used in breeding.

Example 8

In certain examples, RNA interference (RNAi) can be used to reduce or silence expression of a target gene. RNAi can be manifested through stably integrated transgenes, as described herein, through application of RNAi constructs to a plant, such as through a topical application of a formulation to the leaves of a growing plant, and/or through other methods. The target gene and its attributes (such as a DNA sequence) are preferably known in order for RNAi to be effective. In this example, the target gene for RNAi can be grapevine anthocyanin biosynthesis genes, other than VvMybA1.

For example, *Vitis vinifera* Teroldego is a black-fruited, perfect-flowered bunch grapevine variety. RNAi constructs can be developed to target a glutathione S-transferase gene in Teroldego to reduce or silence the expression of this gene. With the glutathione S-transferase gene expression reduced, the result can be a qualitative reduction in anthocyanin in the mature fruit. The RNAi constructs can be applied to the fruit 30 and 60 days after bloom with a band application to the fruiting zone from a tractor-mounted sprayer and the result can be silencing of the glutathione S-transferase gene leading to a qualitative reduction in mature fruit color manifested as white fruit color due to a genetic change in the expression of a non-VvMybA1 gene. The phenotype change in the fruit may not be permanent with this RNAi approach. For example, the fruit or plant may need to be treated at least once per season in order to change the expression of the gene to create a new, desired phenotype. The changes in phenotype caused by applied RNAi may not be integrated into the genome and/or may not be transmitted to progeny asexually or sexually.

Example 9

In some instances, mutagenesis can be used to create a white-fruited perfect-flowered bunch grapevine due to genetic variation not in VvMybA1. The goal of mutagenesis can be to create permanent changes in a grapevine genome that produce a beneficial change in phenotype. The method of mutagenesis can involve exposing the grapevine genome to an agent that is capable of inducing changes in the genome and then growing plants from the cells that have genetic mutations. Different agents can be used in mutagenesis to cause the DNA changes in the genome, such as chemicals (e.g., ethyl methanesulfonate (EMS) or ribonucleoproteins) or radiation (e.g., gamma-rays or X-rays). Different life stages or parts of a grapevine can be used as targets for mutagenesis, and some mutagenic agents or methods of inducing mutations can be more effective than others for particular life stages or grapevine parts. Seeds, seedlings, tissue culture, pollen, buds, and other life stages and grapevine parts can be suitable.

For example, grapevine seeds or seedlings from controlled crosses or open pollination can be the target for mutagenesis. Dormant seeds, sprouted seeds, or seedlings can be exposed to EMS (or other chemicals) by soaking or can be treated with gamma rays (or other radiation). In some implementations, a seedling population that is a cross of *Vitis vinifera* Ruby Cabernet and *Vitis vinifera* Durif may ordinarily be expected to show only black-fruited seedlings. The seeds from this cross can be exposed to radiation and then cultivated. The vines can be examined once they are bearing fruit to determine if there are any white-fruited, perfect-flowered individuals. Pollen can be treated with mutagens and used to create seedling populations that can be screened at fruit-bearing maturity.

Additionally or alternatively, grapevine buds can be treated with mutagens and then propagated and cultivated, and the resulting mature vines can be examined for qualitative white-fruited mutants caused by genetic variation in non-VvMybA1 genes. Grapevine buds can be treated while attached to a plant, such as by applying chemical mutagens to a cotton swab packed around an axillary bud, or grapevine buds can be treated on a cutting, such as a budstick for grafting. For example, Vitis vinifera Lambrusco is a black-fruited, perfect-flowered variety. Lambrusco cuttings can be exposed to radiation (e.g., 80 Gy gamma radiation) and then each bud can be grafted to a rootstock, planted into a vineyard, and cultivated until the mature fruit can be characterized to identify desired white-fruited mutants.

In some instances, grapevine tissue cultures can be treated with mutagens. The tissue cultures can include protoplasts, somatic embryos, embryogenic cultures, organogenic cultures, microcuttings, excised organs, or other kinds of tissue cultures. The tissue cultures can be exposed to the mutagens and then whole vines can be grown from the tissue cultures to evaluate the vines for changes to the trait of interest. In certain examples, the change of interest is a mutation in a perfect-flowered black-fruited vine that creates a qualitative change in fruit color to white due to genetic variation in a gene other than VvMybA1. For example, Vitis vinifera Merlot is a black-fruited, perfect-flowered variety. Embryogenic cultures of Merlot can be exposed to EMS. The embryos can then be cultivated and regenerated into vines, which can then be cultivated to fruit-bearing maturity. The vines can be examined to determine the mature fruit color.

For any mutagenesis method, the mature vines can be inspected after mutagenesis has been conducted on seeds, seedlings, tissue cultures, etc. to determine the flower type (perfect-flowered or pistillate) and to determine the fruit color (black-fruited or white-fruited). Some vines may have homozygous mutations in the anthocyanin biosynthesis pathway that can result in white fruit. In other cases, the vines may be heterozygous for recessive mutations in non-VvMybA1 genes of the anthocyanin biosynthesis pathway that can be revealed through color segregation in seedling populations grown from seeds collected from self-pollinated flowers. Once the phenotypic change is validated to be due to genetic variation not in the VvMybA1 gene, as described herein, the white-fruited, perfect-flowered vines can be cultivated, propagated asexually, and/or used in breeding.

When the target gene in the grape anthocyanin biosynthesis pathway is known and characterized, the sequence can be examined in the grapevines after mutagenesis to determine if the desired changes have been made. For example, Vitis vinifera Graciano is a perfect-flowered, black-fruited variety. EMS can be applied to Graciano vines or cells in an effort to create mutations specifically in the glutathione S-transferase gene (or other relevant genes) that may be expected to result in a qualitative reduction in mature fruit anthocyanin, for example, to create a white-fruited, perfect flowered grapevine. After the mutagenesis is complete, the sequence of the glutathione S-transferase gene in the Graciano cells can be analyzed to determine if mutations are present that reduce or silence the gene and cause the white-fruited phenotype. The plants with the new mutations of interest can be cultivated, propagated asexually, and/or used in breeding.

If the target gene in the grape anthocyanin biosynthesis pathway is not known or is poorly characterized, mutagenesis can be used to create changes in the genes and the fruit phenotype can be used to determine if a useful mutation has occurred. For example, Vitis vinifera Lagrein is a perfect-flowered, black-fruited variety. EMS can be applied in an effort to create mutations in any genes of the anthocyanin biosynthesis pathway, preferably other than VvMybA1. Homozygous mutations in any of these genes would be expected to create a perfect-flowered, white-fruited new variety. After the mutagenesis is complete, the new Lagrein vines can be cultivated to maturity and inspected for mature fruit color. When a homozygous mutation is created in a gene in the anthocyanin biosynthesis pathway other than VvMybA1, the vines with the homozygous mutation can be white-fruited and perfect-flowered. Such grapevines can be identified through visual inspection as having white fruit at maturity, in contrast to the original Lagrein which is black-fruited. In some instances, it may not be necessary to know the gene identity or function in order to create a useful white-fruited vine genetic mutation that is different from VvMybA1 genetic variation.

At least two approaches can be used to validate that any of these white-fruited vines from this mutagenized Lagrein lineage owe their fruit color to genetic variation in a non-VvMybA1 gene. For example, the vines can be crossed or hybridized to a grapevine variety known to have white fruit due to a VvMybA1 mutation in a complementation test. The VvMybA1 mutation is the common type of mutation causing white fruit in Vitis vinifera and in bunch grapes in general, so there are many varieties that can be used in this complementation test (e.g., Muscat of Alexandria or Chardonnay). When the seedlings from the cross of the new white-fruited vine (Lagrein-derived in this example) with the VvMybA1 mutant white-fruited vine are black-fruited, as described herein, this is an example of genetic complementation and indicates that the new white-fruited vines have a genetic change in a gene other than VvMybA1. Another approach is to sequence all of the genes of the anthocyanin biosynthesis pathway, examine the gene expression in the new white-fruited vines, and compare the sequence and expression with VvMybA1 mutant white-fruited vines. These methods are not exclusive and may be used in combination.

Example 10

In various implementations, the white-fruited perfect-flowered bunch grapevines described herein can be used in agriculture, food, and winemaking. The grapevines can provide novel, positive attributes for people who consume grape products, such as wine, juice, raisins, and fresh grapes. The visual color impact of variation at genes other than VvMybA1 can be exemplified by an attractive fresh fruit color of bronze (e.g., non-colored, white) muscadine grapes. Bronze muscadines are quite distinct in color from white bunch grapes, such as Thompson Seedless. Using the methods described herein, similar eye-catching colors can be integrated into beautiful golden seedless bunch grapes, introducing an entirely new color class for table grapes.

Figure 2:
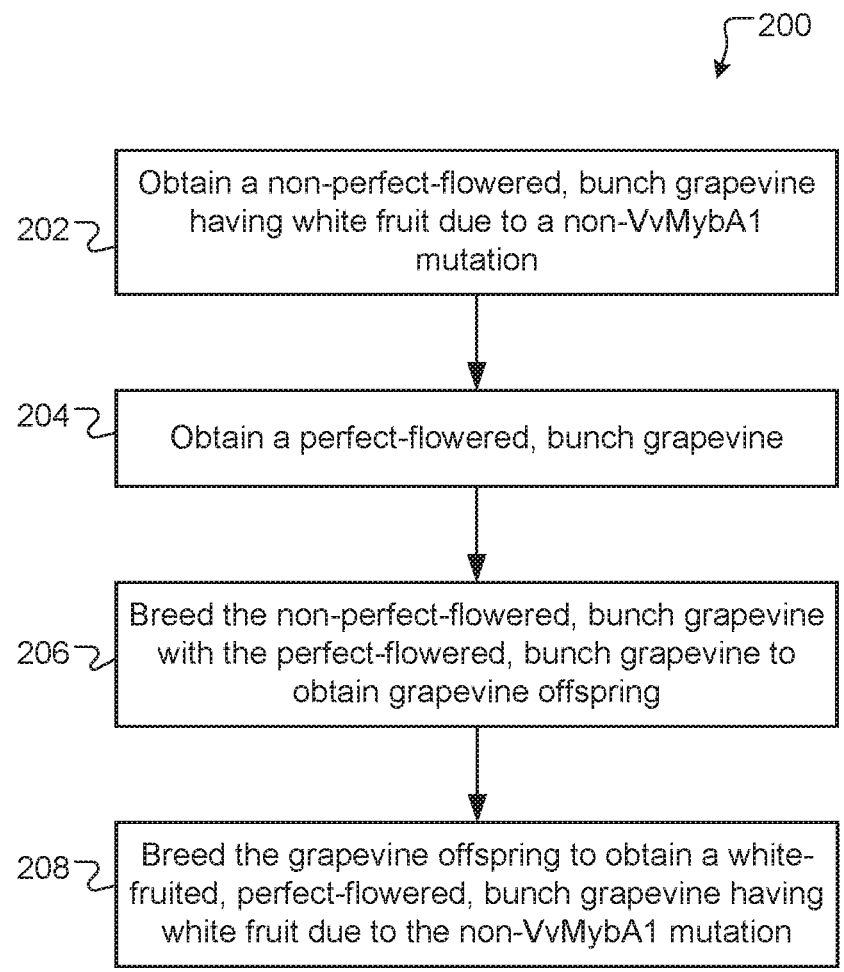
FIG. 2 is a flowchart of a method of producing a white-fruited, perfect-flowered, bunch grapevine having white fruit due to a non-VvMybA1 mutation, according to an exemplary embodiment.

FIG. 2 is a flowchart of an example method 200 of producing a grapevine. A non-perfect-flowered, bunch grapevine having white fruit due to a non-VvMybA1 mutation is obtained (step 202) and a perfect-flowered, bunch grapevine is obtained (step 204). The non-perfect-flowered, bunch grapevine is bred (step 206) with the perfect-flowered, bunch grapevine to obtain grapevine offspring. The grapevine offspring is bred (step 208) to obtain a white-fruited, perfect-flowered, bunch grapevine having white fruit due to the non-VvMybA1 mutation. The resulting white-fruited, perfect-flowered, bunch grapevine can be cultivated, propagated asexually, and/or used in breeding. The resulting white-fruited, perfect-flowered, bunch grapevine can be used to produce a commodity plant product, such as, for example, whole grapes, raisins, wine, juice, fruit leather, paste, puree, freeze-dried fruits, nutraceutical preparations, jam, or jelly. In some instances, the white-fruited, perfect-flowered, bunch grapevine can be produced through mutagenesis, recombinant DNA, and/or gene editing to alter at least one gene in an anthocyanin biosynthesis pathway of a precursor grapevine, such as a black-fruited, perfect-flowered, bunch grapevine.

It is widely reported in the scientific literature that crosses of white-fruited bunch grapevines invariably produce exclusively white-fruited offspring. For example, the *Vitis* International Variety Catalogue indicates that validated parentages of white-fruited bunch grapevines crossed with other white-fruited bunch grapevines (e.g., a Riesling crossed with Silvaner, or a Riesling self-pollination) exclusively produce white-fruited offspring. Surprisingly, and contrary to such reporting, however, the methods described herein have been found to repeatedly and reliably produce exclusively black fruited bunch grapevines from crosses of white-fruited bunch grapevine parents, consistent with the examples described herein. Further the resulting black fruited bunch grapevine can be bred to produce white-fruited, perfect-flowered, bunch grapevines, as described herein, which have white fruit due to a non-VvMybA1 mutation. The non-VvMybA1 mutation that results in the white fruit can be located at any possible location in the grape genome, for example, other than the location of VvMybA1. The non-VvMybA1 mutation can be distinct from and can complement the VvMybA1 mutation or genetic variation. For example, the non-VvMybA1 mutation can relate to or be located in a gene for flavanone 3-hydoxylase that maps to linkage group 4, a gene for chalcone isomerase that maps to linkage group 13, and/or a gene for dihydroflavonol 4-reductase that maps to linkage group 18. Each of the locations for these genes can be different from the location of VvMybA1 on linkage group 2.

In bunch grapevines, white fruit can be caused by a practical or actual absence of anthocyanin pigments. White-fruited bunch grapevines can be favored for the production of white wine (e.g., Chardonnay and Sauvignon blanc are white-fruited, bunch grape varieties) and white unfermented grape juice (e.g., Niagara is a white-fruited bunch grape variety). White grapes can be eaten fresh (e.g., Princess and Autumn King are white-fruited bunch grape varieties) and white grapes can be made into raisins (e.g., Fiesta and Selma Pete are white-fruited bunch grape varieties). In general, white-fruited bunch grape varieties are a well-recognized type that is appreciated and sought by consumers because of the distinct properties of products made from white-fruited bunch grapevines, compared to the properties of products made from black-fruited or colored (e.g., black or red) bunch grapevines.

Further, differences in grape chemical composition can be a primary driver for differences in wine chemical composition. Black grapes can be used to make red wine, and sensory descriptions for red wines typically refer to black, blue, and/or red fruits, such as blackberries, cherries, plums, or pomegranates. In contrast, white grapes can be used to make white wines, and sensory descriptions for white wines typically refer to white or yellow fruits, such as pears, peaches, apricots, or nectarines. While black grapes and white grapes are visually categorized on the basis of anthocyanin content, it is presently discovered that there is a noticeable difference in aroma and flavor composition between red and white wines that is not directly associated with anthocyanin content. For example, the anthocyanin itself may not have an aromatic or flavor impact in grapes or wine. This indicates that the genes (e.g., VvMybA1) or proteins of the anthocyanin production pathways in grapes can also impact grape and wine flavor and aroma, in addition to color.

Advantageously, unlike other white-fruited bunch grapevine varieties (e.g., Chardonnay and Riesling), which have white fruit due to VvMybA1 mutation, the white-fruited grapevines described herein have white fruit due to non-VvMybA1 mutation, and this difference in genetic makeup is able to achieve a new and different relationship between fruit color and aroma and flavor. For example, in some instances, the grapevines described herein can be used to produce white wines that taste like red wines or that have a strong blackberry or cherry aroma. Additionally or alternatively, the methods described herein can be used to change grape color (compared to a parent grape variety), without making any noticeable or significant changes to other grape characteristics, which may influence aroma and/or flavor. Such qualities may be achieved because the grapevines from which the grapes are harvested have white fruit due to a mutation on a different linkage group or location in the grape genome.

Additionally or alternatively, the new grapevines and color mutations described herein can be used to achieve a different visual appearance to fresh grapes that can be appealing for consumers. For example, the difference between purple and bronze fruit color in muscadine grapevines may be driven by genetic variation on linkage group 4. A bronze or golden fruit color is distinct from purple-fruited muscadines and from white-fruited bunch grapes, such as Thompson Seedless, Autumn King, or Princess, which tend towards green, yellow, or amber, due to genetic variation in VvMybA1. Novel table grape varieties with bronze or golden fruit color may be an attractive option for consumers.

Terminology

The phraseology and terminology used herein is for the purpose of description and should not be regarded as limiting.

The term "approximately", the phrase "approximately equal to", and other similar phrases, as used in the specification and the claims (e.g., "X has a value of approximately Y" or "X is approximately equal to Y"), should be understood to mean that one value (X) is within a predetermined range of another value (Y). The predetermined range may be plus or minus 20%, 10%, 5%, 3%, 1%, 0.1%, or less than 0.1%, unless otherwise indicated.

The indefinite articles "a" and "an," as used in the specification and in the claims, unless clearly indicated to the contrary, should be understood to mean "at least one." The phrase "and/or," as used in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The use of "including," "comprising," "having," "containing," "involving," and variations thereof, is meant to encompass the items listed thereafter and additional items.

Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements.

Each numerical value presented herein, for example, in a table, a chart, or a graph, is contemplated to represent a minimum value or a maximum value in a range for a corresponding parameter. Accordingly, when added to the claims, the numerical value provides express support for claiming the range, which may lie above or below the numerical value, in accordance with the teachings herein. Absent inclusion in the claims, each numerical value presented herein is not to be considered limiting in any regard.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. The features and functions of the various embodiments may be arranged in various combinations and permutations, and all are considered to be within the scope of the disclosed invention. Accordingly, the described embodiments are to be considered in all respects as only illustrative and not restrictive. Furthermore, the configurations, materials, and dimensions described herein are intended as illustrative and in no way limiting. Similarly, although physical explanations have been provided for explanatory purposes, there is no intent to be bound by any particular theory or mechanism, or to limit the claims in accordance therewith.

What is claimed is:

1. A method of producing a grapevine, the method comprising:
   breeding a first grapevine with a second grapevine to produce grapevine offspring,
      wherein the first grapevine is a non-perfect-flowered, bunch grapevine having white fruit due to a non-VvMybA1 mutation, wherein *Vitis labrusca* Alba comprises the non-VvMybA1 mutation, and
      wherein the second grapevine is a white-fruited, perfect-flowered, bunch grapevine; and
   breeding the black-fruited grapevine offspring of said first and second grapevine to obtain a white-fruited, perfect-flowered, bunch grapevine having white fruit due to the non-VvMybA1 mutation.

2. The method of claim 1, wherein the first grapevine is pistillate-flowered.

3. The method of claim 1, wherein the first grapevine is *Vitis labrusca* Alba.

4. The method of claim 1, wherein the second grapevine is Muscat of Alexandria, Chardonnay, Thompson Seedless, Princess, Emerald Seedless, Emerald Riesling, Seyval blanc, Cayuga White, Selma Pete, Malvasia bianca, Sauvignon blanc, Chenin blanc, Monbadon, Airen, Melody, Himrod, Romulus, Frontenac blanc, Perlette, Delight, Gold, Lake Emerald, Aligote, Pinot blanc, Villard blanc, Vidal blanc, Canada Muscat, Triplett blanc, Muscat blanc, DOVine, Fiesta, Autumn Seedless, Fuji Muscat, Baco blanc, Centennial Seedless, Dakapo, Ruby Cabernet, or Ruby Seedless.

5. The method of claim 1, wherein the black-fruited grapevine offspring is a perfect-flowered, bunch grapevine.

6. The method of claim 1, wherein each breeding step is independently selected from one of hybridization, cross pollination, self-pollination, or open-pollination.

7. The method of claim 1, wherein breeding the grapevine offspring comprises breeding the grapevine offspring with the first grapevine.

8. The method of claim 1, wherein breeding the grapevine offspring comprises self-pollination or crossing the grapevine offspring with a sibling of the grapevine offspring.

9. The method of claim 1, further comprising reproducing the white-fruited, perfect-flowered, bunch grapevine from at least one of a seed, a cutting, a graft, an air layer, or a tissue culture.

10. A method of producing a commodity plant product, the method comprising:
    obtaining a white-fruited, perfect-flowered, bunch grapevine having white fruit due to a non-VvMybA1 mutation according to the method of claim 1, or a part thereof; and producing the commodity plant product from the plant or a portion thereof,
wherein the commodity plant product comprises at least one of whole grapes, raisins, wine, juice, fruit leather, paste, puree, freeze-dried fruits, nutraceutical preparations, jam, or jelly.

* * * * *